United States Patent

Van Bockel

[11] Patent Number: 6,159,156
[45] Date of Patent: Dec. 12, 2000

[54] PRESSURE SENSOR FOR USE IN AN ARTERY

[75] Inventor: J. Hajo Van Bockel, Leiden, Netherlands

[73] Assignee: Rijksuniversiteit Leiden, Leiden, Netherlands

[21] Appl. No.: 09/134,746

[22] Filed: Aug. 14, 1998

[30] Foreign Application Priority Data

Aug. 15, 1997 [EP] European Pat. Off. ............. 97202523

[51] Int. Cl.$^7$ .................................................... A61B 5/02
[52] U.S. Cl. ........................................... 600/485; 600/481
[58] Field of Search .................................. 600/481–486; 128/903, 897–898, 899

[56] References Cited

U.S. PATENT DOCUMENTS 4,846,191 7/1989 Brockway et al. ..................... 128/903
5,566,676 10/1996 Rosenfeldt et al. ..................... 600/485
5,743,267 4/1998 Nikolic et al. ........................... 600/483

FOREIGN PATENT DOCUMENTS 0 646 365 A1 4/1995 European Pat. Off. .
WO 83/03348 10/1983 WIPO .

*Primary Examiner*—Cary O'Connor
*Assistant Examiner*—Michael Astorino
*Attorney, Agent, or Firm*—Trask Britt

[57] ABSTRACT

Device for introduction into a human or animal body, especially into an artery, specifically to be positioned in an aneurysmal sac in an artery between the wall of the artery and the wall of an endoprosthesis, comprising at least a pressure sensor and a transponder for wireless transmitting data available from the pressure sensor.

4 Claims, 3 Drawing Sheets

PRESSURE SENSOR FOR USE IN AN ARTERY

TECHNICAL FIELD

The invention relates to a device for introduction into a human or animal body, especially into an artery for use as a pressure sensing device.

BACKGROUND

In the arteries of human and animal bodies one of the major problems is the loss of strength of the wall of said arteries, which can result in aneurysm formation. An aneurysm may endanger the health of said human or animal because of the risk of internal bleeding which often results in death of the patient. Therefore, aneurysms are usually treated before rupture occurs by vascular protheses which replace the said aneurysmal artery and thus excluding said aneurysm from the circulation.

A new development is the treatment by a so-called endoprosthesis.

Such endoprotheses are well known to the person skilled in the art and can for example be positioned within said artery by means of a number of stents. Although the procedure can be safely performed now, endoleakage is still a major problem immediately following the operation as well as many months following surgery. Endoleakage is the incomplete sealing of the arterial by the endoprosthesis. Endoleakage can result in a pressure build-up within the aneurysmal sac, enclosed between the wall of said artery and the endoprotheses. Monitoring endoleakage is universally performed by visualisation of the endoleakage by means of for example a CT-scan magnetic resonance, duplex ultrasound and the like. Unfortunately, failure to visualise an endoleak does not exclude the presence of such an endoleak. Also without a visible endoleak, the aneurysmal sac can still be under pressure with the danger of ultimate rupture and said internal bleeding. Failure to visualise endoleakage can for example result from failure to introduce sufficient contrast. fluid into said aneurysmal sac, which has been filled with a thrombus. This will mean that either no or a relatively small amount of blood will leak into the aneurysmal sac, resulting in pressure (without flow) to the arterial wall which may result in said rupture. Of course, measuring pressure would be an ideal test to evaluate the absence of an endoleak. However, because of the invase character of pressure measurement, direct pressure measurements can only be obtained during the operation.

DISCLOSURE OF THE INVENTION

The present invention includes a device for measurement of the pressure within a human or animal body, more specifically in an artery, especially in an aneurysmal sac in an artery between the wall of the artery and the wall of an endoprotheses. To that effect, a device according to the present invention is characterized by the features of claim 1.

In this application arteries have to be understood broadly, including at least arteries, veins and other blood vessels.

A device according to the present invention can be introduced into a human or animal artery, especially into an aneurysmal sac. The pressure sensor can provide pressure related data which can be transmitted to a receiving means outside the human or animal body by means of the transponder. Wireless transmitting of said data has the advantage that it is not necessary to provide for wires extending from the pressure sensor to the skin of said animal or human. Every time when it is indicated the pressure data can be obtained from said pressure sensor. These data can be used for the evaluation of pressure that may still be (or has been developed again) within the aneurysmal sac. Thus, it is useful for assessment of the state of said artery and the risks of possible rupture of said aneurysm. The device is preferably energised by means of an electrical and/or magnetic field, energising the device through said transponder. This means that it will not be necessary to provide said device with a battery, enhancing the safety of the human or animal and prolonging the time of use of the device.

In a preferred embodiment a device according to the present invention is characterized by the features of claim 2.

Introduction of the device into an artery through a catheter has the advantage that only a very small operation is necessary for introduction of the device. A catheter can for example be introduced into the artery by using a hollow needle which can be introduced into an artery in for example a leg. Subsequently, through this catheter the device can be introduced and directed to the proper position. The device can be pushed through the same catheter into position as the endoprosthesis, which is used for treatment of the aneurysms if necessary. This will render major operation or additional unnecessary.

In a further advantageous embodiment a device according to the present invention is further characterized by the features of claim 5.

Means for storing data, connected to at least the transponder, provides for the possibility for storing data taken from the pressure sensor over a prolonged period. Recording such data makes it very easy to obtain information about the occurrence of pressure differences and changes within the artery in said period of time, without the necessity of numerous and repetitious measurements by means of said magnetic or electric field and said transmitting and receiving means.

In a preferred embodiment a device according to the present invention is characterized by the features of claim 6.

Means for positioning the device in a stabile position within the artery, especially within an aneurysmal sac, makes easy and stabile, secure positioning of the device possible. Such positioning has the advantage that the device will not change its position, at least not significantly, thus enabling even better recording of said pressure data. Comparison of the data will therefore be even better possible.

The invention furthermore relates to a set of a device according to the present invention and an endoprostheses, more specifically an endovascular prostheses for use in the abdomen.

Prevention of rupture of aneurysmal sacs is especially vital within the abdomen of human and animal bodies. Internal bleeding, especially within the abdomen can very easy and quickly lead to the death of said human or animal. Thus adequate recording of the pressure in such aneurysms can be lifesaving.

In a further preferred embodiment a set according to the present invention is further characterized by the features of claim 13.

Means for exciting the transponder when positioned in an artery and means for reading the data transmitted from the device to the outside of said human or animal body enables easy and non-invasive measurement of the pressure within the human body, especially in an aneurysmal sac in an artery. Such measurements will provide proper and accurate data about the state of said artery, which can be vital to the human or animal life.

The present invention further relates to the use of a miniaturised pressure sensor and transponder attached thereto, for introduction into a human or animal artery.

The invention further relates to a method for measuring pressure in an artery of a human or animal body, especially in an aneurysmal sac therein, characterized by the features of claim 15.

Use of a method according to the present invention enables easy and accurate measurement of the pressure within said artery, without the necessity of massive operation or repetitive scanning of the relevant parts of said body, comprising contrast fluids or the like. A method according to the present invention is thus both patient friendly and cost effective for the animal or human.

In a preferred embodiment a method according to the present invention is characterized by the features of claim 16.

The pressure sensor and transponder as well as the endoprotheses can be brought into position by using a catheter, introduced through a hollow needle or the like. Such operation is non-traumatic and can quickly, easily and accurately be performed.

Furthermore, the present invention relates to the use of a catheter for introduction of a sensor and a transponder into a human or animal body.

BRIEF DESCRIPTION OF THE DRAWINGS

To further clarify the invention, exemplary embodiments of a device and a set according to the present invention will be described hereafter, with reference to the drawings.

In the description corresponding parts have corresponding reference signs. Measurements and values, as well as the specific embodiments are merely presented as examples and are not to be interpreted as limiting the scope of the present invention.

BEST MODE OF THE INVENTION

Figure 1:
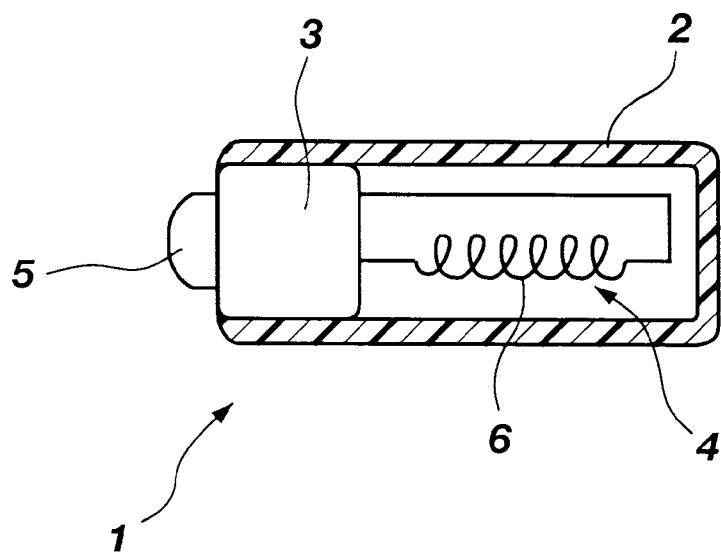
FIG. 1 schematically shows a pressure sensing device according to the present invention, for introduction into a human or animal artery, in a first embodiment.

FIG. 1 shows, at an enlarged scale and in cross-section, a device for introduction into a human or animal artery for use as a pressure sensing device. The device 1 comprises a housing 2, preferably made of biocompatible plastic and air and liquid tight. The housing 2 encloses a pressure sensor 3, connected to a transponder 4. The pressure sensor means 3 comprises a pressure sensing element 5, extending at least partly outside the housing 2. The pressure sensing element can be of any suitable type, for example piezo-electric, membrane, strain gauge or capacity operated or the like. The measurement range has to be sufficient to measure normal and high pressures in said artery. For example, a measurement range for use in a main artery could be from 0 to 220 mm Hg ($29.3*10^3$ Pa) more specifically 50–150 mm Hg ($6.67*10^3 – 20*10^3$ Pa). A suitable range and sensitivity of the pressure sensing element 5 can be readily chosen by the person skilled in the art.

The transponder 4 comprises in the embodiment as shown in FIG. 1 a coil 6, to be energized by an external electromagnetic field, inducing the transponder 4 to transmit a signal, carrying data obtained from the pressure sensing means 3. The signal transmitted by the transponder 4 can be received outside the human or animal body, the pressure data thus readily available for interpretation by means of for example a suitable computer or the like. Under circumstances it can be sufficient to assess whether the pressure within said artery is higher or lower than a boundary pressure, in which case the data can be transformed to an on/off signal for for example a LED. The form of the transponder depends inter alia on the intended use of the device, especially the intended position during use and the relevant animal or human body. Appropriate choices will be readily understood by the person skilled in the art.

Figure 4:
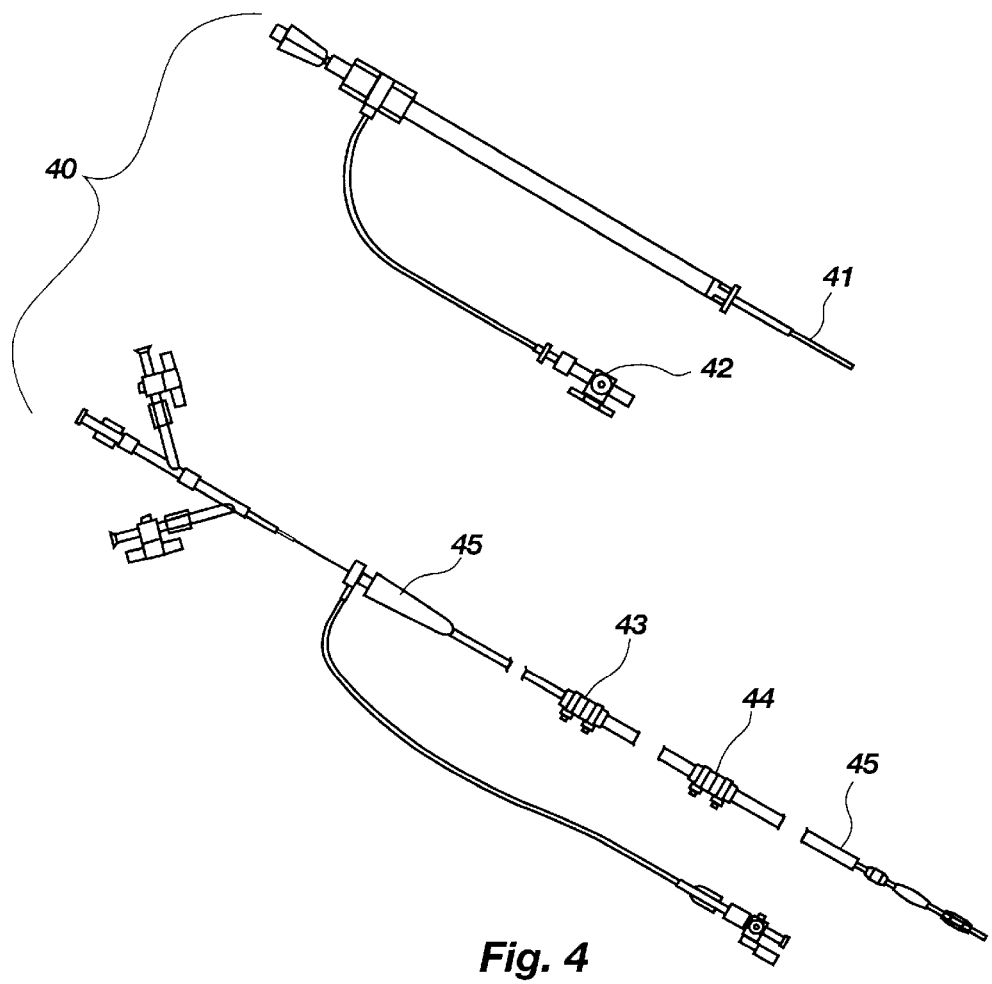
FIG. 4 shows a catheter for introduction of a pressure sensing device and an endoprosthesis into an artery of a human or animal body.

By miniaturization a device according to the present invention is made suitable for introduction into an artery, using a standard or specialized catheter 40 as shown for example in FIG. 4, comprising i.a. a guide tube 41, a stop cock 42, appropriate pushers 43 and 44 stop valves 45 and outer sheath 45 and the like. In FIG. 1, the outer dimensions of the housing 2 are for example 1 to 3 mm in diameter and 2 to 4 mm in length. However, the outer dimensions can be chosen depending on the position within said animal or human body. These methods and means are well known to a person skilled in the art.

Figure 2:
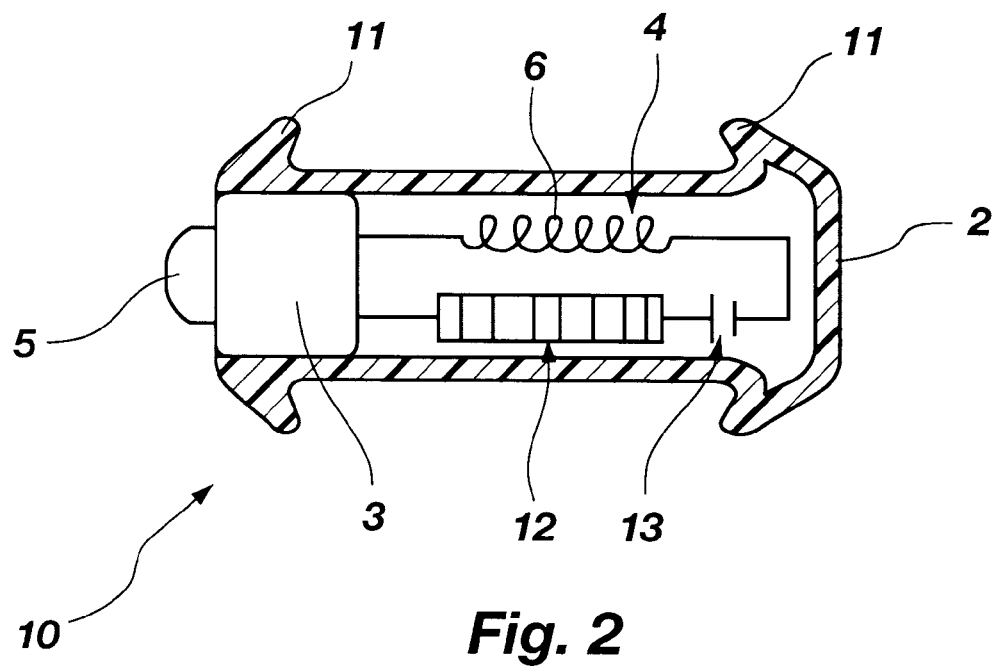
FIG. 2 schematically shows a pressure sensing device according to the present invention, in a second embodiment.

FIG. 2 shows an alternative embodiment of a device according to the present invention.

In this embodiment a device 10 comprises hook or ring shaped elements 11 extending from the outside of the housing 2, which elements 11 are suitable for obtaining a stable position of the device 10 within for example clogged blood in an aneurysmal sac or to an endoprosthesis, as will be explained later in connection with FIG. 3. In the embodiment as shown in FIG. 2 the pressure sensor means 3 are again connected to a transponder 4, comprising for example a coil 6 for energizing the device and transmitting data to the outside of said animal or human body. Furthermore the device 10 comprises data storage means 12 and energy means 13, for example a capacitor or a battery. The capacity of the energy means 13 have to be suitable to energize at least the pressure sensor means 3 and the data storage means 12 during a prolonged time span, for example one or more days or weeks. With a device 10 according to FIG. 2, during said prolonged time span pressure data can be obtained at intervals and stored in the data storage means 12. After said time span the transponder can be activated for transmitting the data stored in the data storage means 12, providing data about the actual pressures measured within said artery as well as changes during said prolonged time. In a preferred embodiment the energy means 13 can be energized by means of the transponder 4, using an electromagnetical field. If the data only has to be obtained during a relatively short time after introduction of the device 10 into an artery, a small battery can be sufficient.

Figure 3:
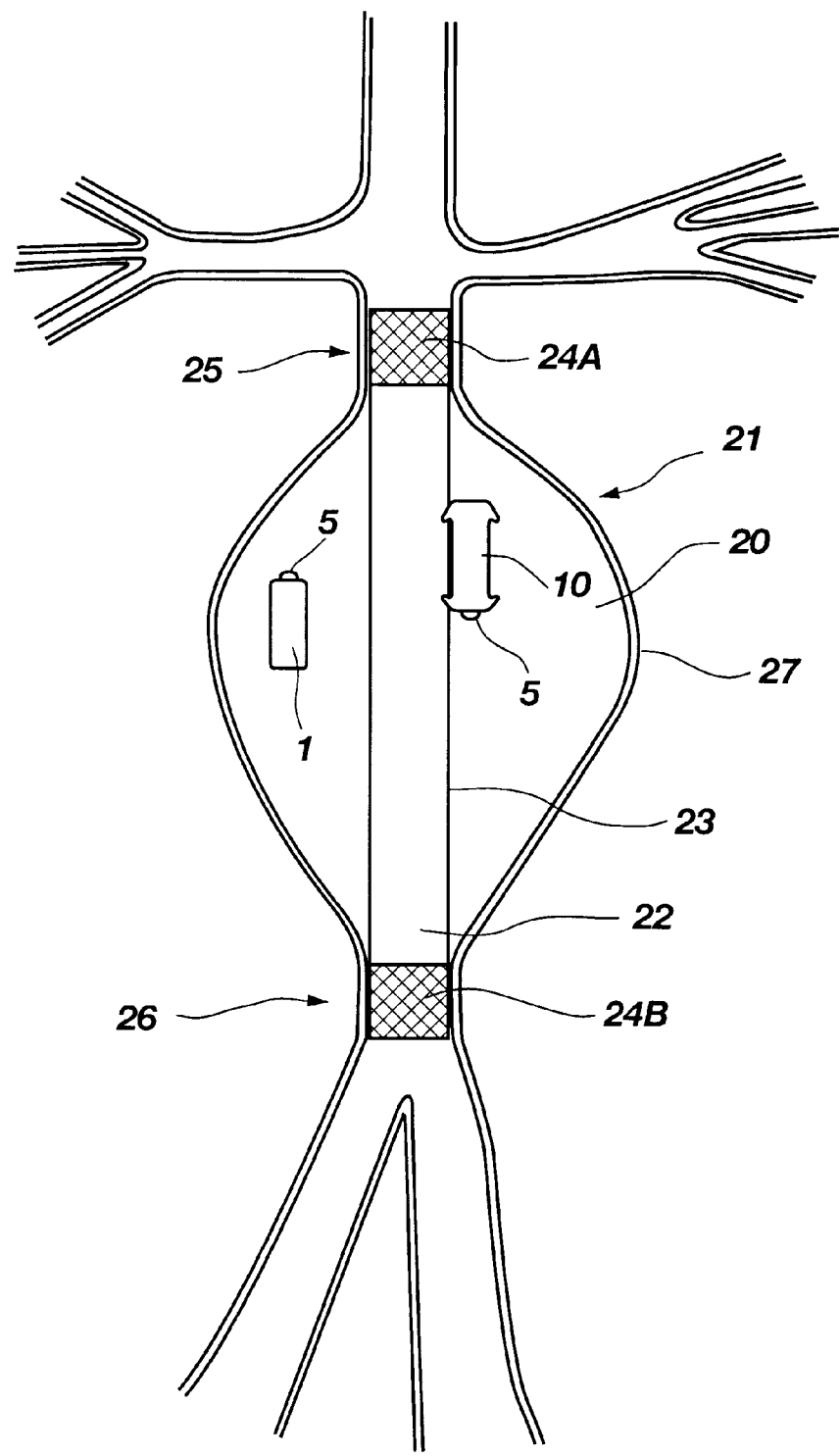
FIG. 3 schematically shows pressure sensing devices according to the present invention, positioned in an aneurysmal sac, excluded from the circulation by an endoprosthesis.

A device 1, 10 according to the present invention is especially suitable for measurement of pressure within an aneurysmal sac 20 in an artery 21, for example an artery in the abdomen of a human body, as shown in FIG. 3.

An aneurysm is dangerous to the health of a human or animal since rupture of especially an artery would lead to internal bleeding with possible lethal consequences. In order to negate this risk endoprosthesis are used for bridging an aneurysm. In FIG. 3 a tube endoprosthesis is shown, positioned within an artery 21. The endoprosthesis 22 comprises a flexible, closed wall 23, and is provided fully or at both ends with a stent 24a, 24b. A first end 25 of the endoprosthesis is positioned within the artery 21 at the upstream side of the aneurysm 20, by means of the stent 24a, the second end 26 at the opposite, downstream side of the aneurysm by means of the second stent 24b. An endoprosthesis of this type is known in the state of the art and is for example manufactured under the registered trademark Vanguard by the Meadox Boston Scientific Corporation, USA. However, all kinds of endoprosthesis can be used, for example a tube, bifurcated, uni- or bilateral prothesis. A device 1, 10 according to the present invention is introduced into the aneurysmal sac 20 between the wall 27 of the aneurysmal sac and the endoprosthesis 22. In FIG. 3 a device 1 according to FIG. 1 is positioned left of the endoprosthesis, within clotted blood in the aneurysmal sac. In the same FIG. 3 a device 10 according to FIG. 2 is positioned within the aneurysmal sac 20, right of the endoprosthesis 22, and is attached to the endoprosthesis by means of the hook means 11. These positions are only shown in one figure for elucidation purposes and might normally not be combined. Other means for positioning a device according to the present invention within an aneurysmal sac or a blood vessel can be used in any suitable manner.

A device according to the present invention can be introduced into an artery, especially into an aneurysmal sac 20, using a catheter 40, for example as shown in FIG. 4, through which also the endoprosthesis 22 with the stents 24a, b can be introduced. Appropriately, first the device 1, 10 is introduced into the clogged blood in the aneurysmal sac 20, after which the endoprosthesis is brought into position and fixated with the stents 24. It is of course also possible to position a device according to the present invention in an artery or other body part during an operation in which at least one incission is made in the body.

Using the device 1, 10 positioned in the aneurysmal sac 20 provides the possibility to monitor any changes in the pressure within the aneurysmal sac 20, which could be an indication of leakage of blood into the aneurysmal sac 20, passing either one of the stents 24a, 24b or endoleak transmitting pressure into the aneurysmal sac 20 without blood transfer. If the pressure measured within the aneurysmal sac 20 becomes too high or changes significantly, correction of the position of the endoprosthesis 22 and/or the stents 24 may be necessary. Since the pressure detection is non-invasive during use and very local, monitoring of a patient's blood pressure after positioning of the endoprosthesis 22 is very easily possible, preferably policlinical. Especially when a device according to FIG. 2 is used, sufficient data can be obtained without undue burden to the human or animal.

Figure 5:
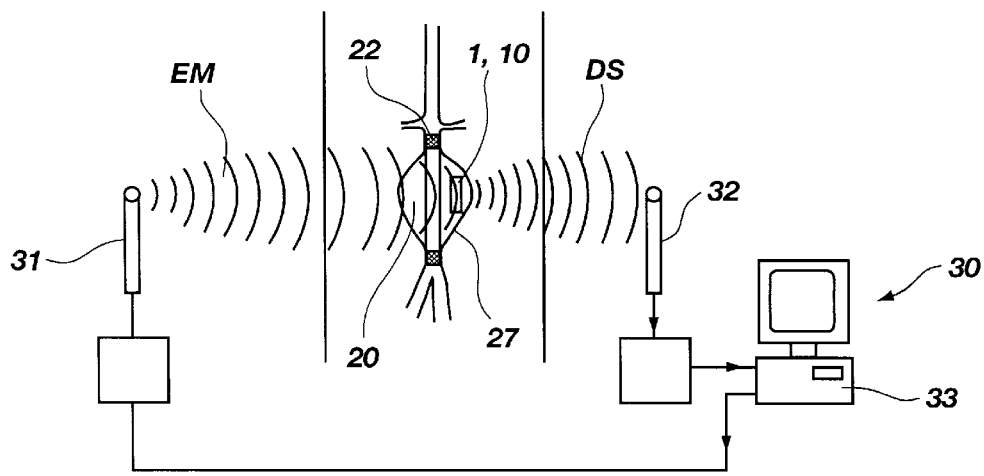
FIG. 5 shows schematically a set according to the invention for reading data measured by the pressure sensing device.

FIG. 5 shows schematically a device for activating the transponder 4 of the pressure sensing device 1, 10 within an aneurysmal sac 20, and for receiving the data signals transmitted by the transponder 4. This device 30 comprises a first antenna 31 for providing an electromagnetic field EM for energizing the transponder 4. Furthermore the device 30 comprises a second antenna 32 for receiving the data signals DS transmitted wireless by the transponder 4. The first antenna 31 and second antenna 32, which can be of any suitable form and dimension and can also be combined in one antenna, are connected to control means, for example a computer 33. The computer program helps to read the data from the data signals and transforming these into readable signals, for example a blood pressure graph on the computer screen or a print out.

In a further embodiment, not shown in the drawings, energy means are provided which can be energized by blood pulses within the artery, resulting from the (normal) heartbeats. This can for example be piezo-electrical means, pressure sensitive membranes or the like, which can generate sufficient energy to at least energize data storage means 12.

The present invention is by no means limited to the embodiments as described in the description and shown in the figures. Many alternatives are possible.

For example other means for introduction of a device into an artery of a human or animal body can be used, whereas a pressure sensing device according to the present invention can also be positioned in other arteries or different parts of the body, with or without an endoprosthesis. Furthermore, more than one pressure sensing device according to the present invention can be introduced into one aneurysmal sac, for example for obtaining data from various positions within said aneurysmal sac. Moreover, different means for positioning of a device according to the present invention within a human or animal body can be appropriately used. A housing of a device according to the present invention can be made of any suitable material and is preferably mainly massive, for example made of biocompatible foam or the like. Each device can be multifunctional, for example comprise further sensor means, such as temperature sensing means, which can be connected with a further transponder having different transponding characteristics.

These and many similar variations are considered to fall within the scope of the present invention.

What is claimed is:

1. A method for using a miniaturized pressure sensor and transponder attached thereto, comprising introducing said miniaturized pressure sensor and transponder into an aneurysmal sac of a human or animal.

2. A method for measuring pressure in an aneurysmal sac of an artery of a human or animal body, comprising positioning a pressure sensor and a transponder attached to the pressure sensor in said aneurysmal sac, the transponder being arranged for wirelessly transmitting pressure data from the pressure sensor to detecting means outside said human or animal body.

3. The method according to claim 2, wherein said positioning comprises introducing the pressure sensor and transponder into said artery by means of a catheter and further comprising introducing an endoprosthesis into said artery in a position over the pressure sensor and transponder, thus enclosing the pressure sensor and transponder within said aneurysmal sac, between the wall of said artery and said endoprosthesis.

4. The method of claim 1, further comprising introducing said miniaturized pressure sensor and transponder into said aneurysmal sac with a catheter.

* * * * *